United States Patent [19]

Kummer et al.

[11] Patent Number: 5,092,891
[45] Date of Patent: Mar. 3, 1992

[54] CEMENT PLUG FOR THE MEDULLARY CANAL OF A BONE AND COACTING TOOL FOR INSTALLING SAME

[76] Inventors: Frederick J. Kummer, 344 82nd St., Brooklyn, N.Y. 11209; Steven A. Stuchin, 955 Park Ave., New York, N.Y. 10028

[21] Appl. No.: 490,711

[22] Filed: Mar. 8, 1990

[51] Int. Cl.$^5$ .......................... A61F 2/28; A61F 5/04
[52] U.S. Cl. ...................................... 623/16; 606/62; 606/63
[58] Field of Search .................... 623/16, 16 A, 23; 606/62, 63

[56] References Cited

U.S. PATENT DOCUMENTS

| | | |
|---|---|---|
| 3,866,248 | 2/1975 | Kummer . |
| 3,987,499 | 10/1976 | Scharbach et al. . |
| 4,011,602 | 3/1977 | Rybicki et al. . |
| 4,245,359 | 1/1981 | Stuhmer . |
| 4,276,659 | 7/1981 | Hardinge . |
| 4,293,962 | 10/1981 | Fuson . |
| 4,302,855 | 12/1981 | Swanson . |
| 4,337,773 | 7/1982 | Raftopoulos et al. . |
| 4,344,190 | 8/1982 | Lee et al. . |
| 4,399,814 | 8/1983 | Pratt, Jr. et al. . |
| 4,447,915 | 5/1984 | Weber . |
| 4,488,549 | 12/1984 | Lee et al. . |
| 4,523,587 | 6/1985 | Frey . |
| 4,562,598 | 1/1986 | Kranz . |
| 4,625,722 | 12/1986 | Murray . |
| 4,627,434 | 12/1986 | Murray . |
| 4,686,973 | 8/1987 | Frisch . |

FOREIGN PATENT DOCUMENTS 0058744 9/1982 European Pat. Off. .......... 623/16 A

OTHER PUBLICATIONS

"Intramedullary Plugs in Cemented Hip Arthroplasty", Gloria M. Beim, BS, Carlos Lavernia, MD, and F. Richard Convery, MD.
"Ceramics as a New Approach to the Improvement of Artificial Joints"; S. F. Hulbert and J. J. Klawitter.

Primary Examiner—David J. Isabella
Assistant Examiner—Debra S. Brittingham
Attorney, Agent, or Firm—Hoffman, Wasson & Gitler

[57] ABSTRACT

A cement plug for sealing the medullary canal of a bone to restrict the flow of cement, debris, etc. beyond a predetermined point in the canal. The cement plug, which is executed in a biocompatible plastic, comprises (1) a tubular body that is a slit axially at three or more locations to define resilient fingers, (2) an obturator plate located at the upper end of the body, (3) a tapered conical plug that can be advanced through the lower end of the body and intot he interior thereof, and (4) a threaded bolt that extends through the tubular body and into the conical plug. Locator holes are formed in the obtrator plate, and sharpe edges, teeth, or locator tab(s) are formed on the outer surface of the conical plug so that said plug does not rotate relative to the tubular body of the plug. An insertion tool, including an inner tube and an outer tube, is engaged within the locator by depending plins. The lower end of the inner tube engages the upper end of the threaded bolt. By rotating a handle so that the tubes move relative to one another, a torquing force is imparted to the head of the bolt. The bolt draws the plug upwardly into the interior of the plug body. Such upward movement of the tapered conical plug forces the resilient fingers outwardly into secure engagement with the wall defining the medullary canal.

Cement, under pressure, is then forced down the medullary canal. The obturator plate, which is situated perpendicular to the body of the plug at the upper end thereof, serves as a barrier to the flow of cement. The obturator plate extends transversely across the medullary canal and may even bow slightly under such pressure; however, the plug will not slip and the cement will now flow, leak or migrate past the plate and adversely impact upon the resilient fingers. The obturator plate may even serve as a secondary gripping member. The plug thus forms a stable platform atop which a prosthesis may be accurately positioned.

19 Claims, 2 Drawing Sheets

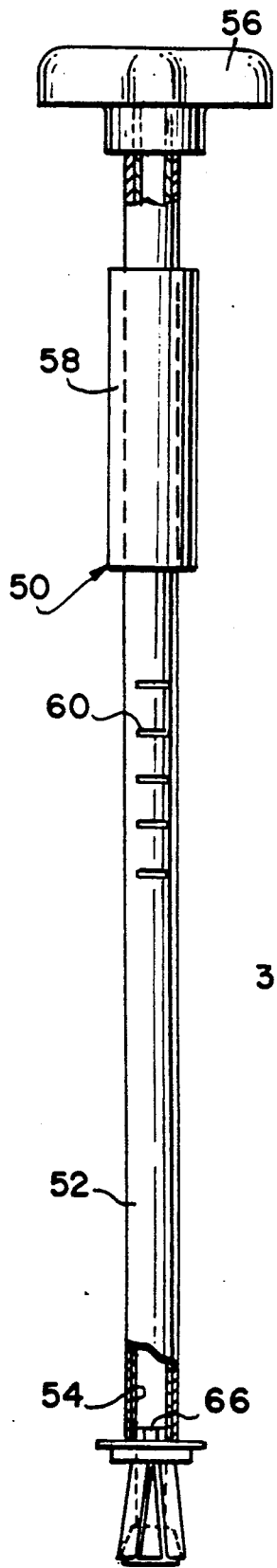
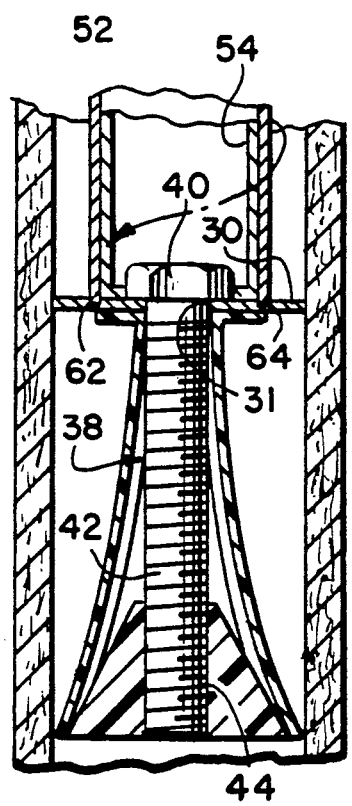
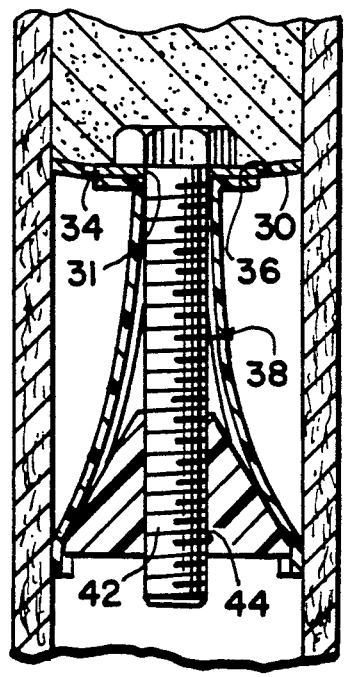
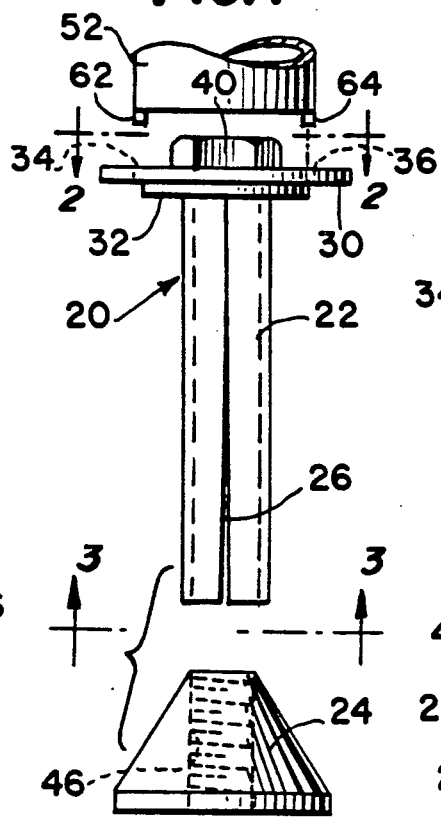
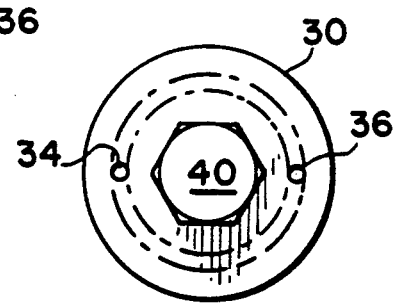
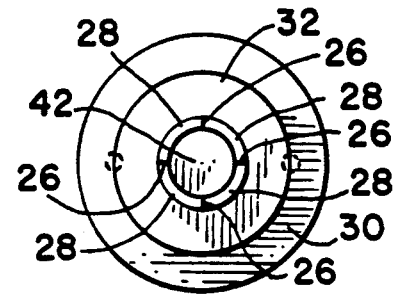
FIG. 4  FIG. 5  FIG. 6
FIG. 1  FIG. 2  FIG. 3

CEMENT PLUG FOR THE MEDULLARY CANAL OF A BONE AND COACTING TOOL FOR INSTALLING SAME

BACKGROUND OF THE INVENTION

The present invention relates broadly to surgical repair or replacement of diseased, or damaged, joints of the human body, and more particularly to cement plugs for sealing the medullary canal of a bone to prevent cement travel therepast.

Replacement of diseased, or damaged, human joints by prosthetic devices is well known. Such prosthetic devices are used to replace defective finger joints, elbow joints, knee joints and hip joints. Frequently, these prosthetic devices include an elongated stem that is inserted into the medullary canal of the bone adjacent to the resected joint. In a hip joint replacement, for example, the elongated stem of a hardened, biologically acceptable metal material is inserted into the medullary canal of the femur, and the ball, or head, of the prosthesis fits into a properly prepared socket in the pelvis of the patient. A plug is positioned within the medullary canal. The plug serves as a barrier to the flow of the cement, beyond a predetermined depth, so that the cement can secure the elongated stem of the prosthetic device at the desired depth within the canal. The cement is typically a curable acrylic polymer cement, such as polymethylmethacrylate, which exhibits a tendency to flow past the plug. Such tendency is exacerbated by the need to inject the cement into the medullary canal under pressure.

Diverse cement plugs for blocking the medullary canal, and thus providing a stable base for the elongated stem of a prosthetic device or the like, are shown in the patented prior art. To illustrate, U.S. Pat. No. 4,302,855, granted Dec. 1, 1981, to Alfred B. Swanson, discloses a bone plug 10 for plugging the medullary canal of a bone to restrict the flow of cement to affix a prosthesis. The bone plug comprises a resilient body of medical grade material, such as silicone polymer rubber. The body has a smooth, blunt, round nose 12, a midportion 14 joined to the nose and having a toroidal shape, and an upper, open ended portion 16 joined to the midportion and defining a recess 18. The upper, open ended portion is generally frusto-conical in shape, and further defines a plurality of circumferentially spaced petal-like elements 36. A manual instrument (FIG. 6) is used to insert the properly sized bone plug, to the correct depth, within the medullary canal, prior to the introduction of acrylic cement, under pressure.

U.S. Pat. No. 4,344,190, granted Aug. 17, 1982 to Alan J. C. Lee and Robin S. M. Ling, discloses an implant that is adapted to locate a hip prosthesis. A push-fit plug 12 fits into the medullary canal 18, and prevents cement from penetrating down the canal. The plug may be formed of a biodegradable material, may have serrations about its midsection for enhanced gripping ability, and may be tapered or conical at its upper end 16. An implant 22 is located above plug 12 and is retained in fixed position by pressurized cement 24.

U.S. Pat. No. 4,276,659, granted July 7, 1981, to Kevin Hardinge, discloses another medullary canal plug. The plug comprises a substantially hemispherical center 10 with a plurality of individual leaves 11 radiating outwardly from the center. The adjacent edges 12 of the leaves are angularly inclined relative to the faces to facilitate the partial overlapping of the leaves, when moved from a planar disposition (shown in FIG. 2) to a frusto-conical position (shown in FIG. 3) during insertion into the medullary canal 15.

U.S. Pat. No. 4,447,915, granted May 15, 1984 to Berhard G. Weber, discloses a medullary canal plug comprising: a deformable and expandable cup-shaped outer body 1 having a jacket formed of a number of segments 3, and a conical expansion body 10 which is pulled, or drawn, into the outer body in order to expand same. The expansion of the outer body causes barb-like anchoring elements 4 to hook into the inner wall 32 of a bone 30. The two bodies 1, 10 are permanently secured together, via serrations 5, 11 on the inside of outer body 10 and on the outside of the expansion body. A tool 20 with an elongated spindle 21 passes axially through the outer body 1 to engage a central bore in the expansion body and draw such body upwardly into the lower, open end of the outer body 1.

U.S. Pat. No. 4,245,359, granted Jan. 20, 1981, to Karl-Gerhard Stuhmet, discloses a plug 3 that is made of a plastic material and functions as a cement barrier for openings produced by an operative procedure in medullated bones 1. The plug is clamped between the side walls of the opening in the bone by elastic flanges 6, 8, which prevent bone cement from escaping downwardly upon inserting a medullary stem. U.S. Pat. No. 4,686,973, granted Aug. 18, 1987 to Elden E. Frisch, discloses an inflatable bone plug that is inflated with a biocompatible fluid, and is deflated in a controlled manner, after the cement hardens. The bone plug may be formed of a container of a silicone elastomer permeable to carbon dioxide gas.

U.S. Pat. No. 4,011,602, granted Mar. 15, 1977, to E. F. Rybicki et al, discloses a porous, expandable device for attachment to bone tissue. The device includes a body member that is slit from opposite ends, and receives a cylinder member 22 therein in response to actuation of threaded bolt 26.

Yet other bone plugs are shown in U.S. Pat. No. 4,293,962, granted Oct. 13, 1981 to Robert L. Fuson; U.S. Pat. No. 4,627,434, granted Dec. 9, 1986, to William M. Murray; and U.S. Pat. No. 4,337,773, granted July 6, 1982, to D. D. Raftopoulus et al.

Despite the variety of bone plugs, which are also known as cement plugs, long term follow-up studies of replacements and repairs have shown that the holding power of conventional plugs has been less than anticipated. Cement migration and leakage has been found to be a persistent problem. Consequently, the failure rate of the surgical repairs and/or replacements for different joints, or at the very least, the loosening of such joints over time, has been far higher than anticipated. Thus, the need for a simple, inexpensive, biocompatible, adjustable cement plug that will fit securely within canals of various sizes and yet function effectively, over prolonged periods of time, remains, at best, only partially met.

SUMMARY OF THE INVENTION

The instant invention contemplates a medullary cement plug that is executed in a non-porous, biocompatible plastic with a minimum of easily-molded components, that is susceptible of installation by a simple, coacting manual tool, and that functions satisfactorily over the life span of the associated prosthetic device. The instant cement plug consists of (1) a tubular body that is slit axially to define resilient fingers at its lower end, (2) an obturator plate located at the upper end of the body remote from the fingers, (3) a tapered conical plug that fits into the lower, open end of the tubular body and can be advanced into the interior of said tubular body, and (4) a threaded bolt that extends through the tubular body and into the tapered conical plug. Locator holes are formed in the obturator plate; such holes do not extend through the plate, lest cement migrate or leak therethrough.

A manually operable tool, including a pair of tubular members, has pins at the lower end of the outer tube that fit into the locator holes, and a recess in the interior tubular member that engages the head of the bolt. By rotating a handle at the upper end of the tool, the bolt draws the conical tapered plug upwardly into the interior of the tubular body while forcing the resilient fingers outwardly to engage the wall of the medullary canal. The obturator plate at the upper end of the plug extends transversely across the medullary canal, and functions as a barrier to prevent pressurized cement and debris, such as tissue, bone chips, etc. from flowing therepast. Even if the plate bows slightly under the pressure of the cement, the plate still functions effectively and the grip of the resilient fingers on the interior of the bone is undiminished. In some circumstances, the obturator plate contacts the wall of the medullary canal and serves as a secondary sealing member.

The tapered conical plug of the present invention has a threaded centrally located, axial bore. The elongated threaded bolt passes through the tubular body of the cement plug and cooperates with the threaded bore within the conical plug. The head of the bolt rests upon the obdurator plate at the upper end of the tubular body. When torque is applied to the head of the bolt in one direction, the conical plug is advanced upwardly along the shank of the bolt until the resilient fingers of the tubular body are firmly engaged with the bone canal. The simple, manually operable tool, described above, delivers torque to the bolt, and the cement plug can be easily installed in the desired location. If further adjustment, or correction, is required, such tool is rotated in a second opposing direction to retract the conical plug so that the fingers can relax and allow the cement plug to be moved to a new location in the medullary canal.

In the preferred embodiment, the tapered conical plug has a smooth, unbroken exterior surface. However, in alternative embodiments, the exterior surface of the conical plug may be interrupted by serrations, sharp corners, or a locator tab, so that the conical plug will not slip and rotate relative to the tubular body. Consequently, the tapered conical plug will only advance axially through the lower end of the tubular body and into the interior thereof, forcing the resilient fingers outwardly into locking engagement with the wall defining the medullary canal.

The tubular body of the present invention is slit axially, from the bottom end of the body toward its upper end, at three, or more, equally spaced parallel locations. The fingers defined in the plastic body between the adjacent slits are sufficiently resilient to flex outwardly and engage the wall of the bone canal. The extent of the flexing movement is well within the elastic memory of the plastic body, so that the fingers can be extended, and retracted, without loss of gripping strength, when the plug is inserted, seated, and then, if required, moved again, to a new position within the bone canal. The extent of the outward flexing of the fingers is such that one plug, of a particular size, can function satisfactorily with a variety of sizes of bone canals. Such capability obviates the need for numerous sizes of plugs, while not sacrificing any of the enhanced operational characteristics of the instant bone plug.

The obturator plate at the upper end of the tubular body, which is annular in shape when viewed from above, may also engage the bone canal and serve as a secondary locking mechanism for the present cement plug. However, more important to the satisfactory performance of the present bone plug, is the ability of the obturator plate to function as a leak-proof barrier to the unwanted travel of pressurized bone cement, and/or other debris. The obturator plate may even flex, or bow, under the load imposed by the pressurized cement, but the edges of the plate maintain continuous contact with the medullary canal and prevents passage, travel, or leakage of bone cement therepast. The obturator plate thus keeps the rest of the bone plug free from bone cement, and the tapered conical plug can be retracted from the tubular body quickly and easily, so that the bone plug can be moved, adjusted, and re-set, without the usual difficulties associated with removing a conventional cement plug, once installed.

As noted previously, a simple, manually operable tool, is employed to install the present plug. Such tool includes an inner tube, an outer tube, and a handle secured to the upper end of the inner tube. Two or more pins may be situated at the lower end of the outer tube, to fit into complementary locator holes in the obturator plate of the plug. The lower end of the inner tube may have a hexagonal recess to engage the bolt head, or it may terminate in a screwdriver blade to engage a slot in the bolt head, if a slotted bolt head is utilized. A gauge is defined on the exterior of the outer tube so that the cement plug is inserted to the desired depth within the bone channel, and then locked into fixed position. A knob, or cross-piece, at the upper end of the inner tube is rotated to provide sufficient torque to rotate the bolt and draw the tapered conical plug into the tubular body of the plug. The resilient fingers defined by the tubular body of the present plug securely engage the bone canal, and facilitate the proper location of the prosthesis within the bone canal.

The location of the obturator plate at the upper end of the tubular body of the cement plug insures that the pressurized cement will not contact and adversely affect the gripping action the resilient fingers. Also, the obturator plate prevents cement from flowing between the gripping fingers, a common problem with known cement plugs.

Numerous other advantages of the present cement plug, and coacting insertion tool, will become readily apparent from a review of the following detailed description of the invention, when construed in harmony with the appended drawings.

BRIEF DESCRIPTION OF THE DRAWINGS

FIG. 1 is an exploded, front elevational view of the cement plug and a fragment of the insertion tool constructed in accordance with the principles of the instant invention;

FIG. 2 is a horizontal, cross-sectional view of the obdurator plate at the top of the tubular body of the cement plug, with the head of a bolt passing therethrough, such view being taken on line 2—2 in FIG. 1 and in the direction indicated;

FIG. 3 is a horizontal, cross-sectional view of the bottom of the tubular body of the cement plug, such view being taken on line 3—3 in FIG. 1 and in the direction indicated;

FIG. 4 is a front elevational view of the insertion tool positioned atop the cement plug;

FIG. 5 is a vertical cross-sectional view of a fragment of the insertion tool, and the cement plug, positioned within the medullary canal, but prior to actuation;

FIG. 6 shows the same relationships as FIG. 5, but the cement plug has been actuated and bone cement has been introduced into the medullary canal;

DETAILED DESCRIPTION OF THE PREFERRED EMBODIMENT

Figure 7:
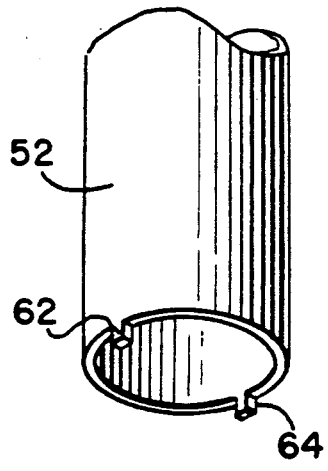
FIG. 7 is a perspective view of the lower end of the outer tube of the insertion tool shown in FIG. 4, such view showing the pins adapted to fit into holes in the obturator plate of the cement plug.

A cement plug constructed in accordance with the principles of the instant invention is shown in FIGS. 1-6, and is identified generally by reference numeral 20. Cement plug 20 is fabricated from a sanitary, non-porous, biocompatible plastic. Two of the components of plug 20 are a tubular body 22 and a tapered, conical plug 24. Other major components include an obturator plate and a threaded bolt for drawing the conical plug into the lower end of the tubular body.

A plurality of axial slits 26 extend from the lower edge of the tubular body upwardly along the greater length of the body 22. A minimum of three parallel axial slits may be defined in the body, although four, five, or six slits may function satisfactorily. In FIG. 3, four slits 26, spaced at 90° intervals, are visible. Resilient fingers 28 are defined between adjacent slits 26. The plug is executed in a plastic that exhibits resiliency within wide limits of stress, so that the fingers can be forced outwardly from the tubular body in response to the entry of the plug 24 into the lower end of the tubular body 22.

An obturator plate 30, which extends perpendicular to the tubular body 22, is formed at the upper end of the body. A central aperture 31 extends through the plate 30, and the aperture is selected to allow the head of a bolt to rest thereon, while the shank extends below the plate 30. A small reinforcing plate 32 may be formed below the plate 30 to reinforce same. Locator holes 34, 36 are formed in the upper surface of plate 30, as shown in FIGS. 1 and 2. Such holes do not extend through the obturator plate 32.

A bolt, indicated generally by reference numeral 38, includes a hexagonal head 40 and an elongated shank 42. The bolt is seated atop plate 30, and extends axially through tubular body 22 and projects below the body. Threads 44 extend along the shank 42, as shown in FIGS. 5 and 6.

Tapered, conical plug 24 fits into the open, lower end of tubular body 22 and drives the fingers 28 outwardly. The outer surface of the plug is smooth and unbroken. A central, axially extending, threaded bore 46 is formed in plug 24. The threads in the interior bore 46 are complementary to, and cooperate with, the threads 44 on the exterior of the shank 42 of the bolt. Consequently, when a torquing or rotational force is applied to head 40 of bolt 38, the plug 24 is drawn into the interior of body 22 and the fingers 28 are forced outwardly. The tapered conical shape of the plug is selected for maximum effectiveness.

Although the instant cement plug 20 could function satisfactorily with known plug installation tools, a simple tool has been developed for maximizing the effectiveness of cement plug 20, and facilitating installation, and removal, thereof from a medullary bone canal. Such tool, which is identified generally by reference numeral 50, is fully illustrated in FIG. 4, while only the lowermost portion thereof is shown, in an enlarged scale, in FIG. 5.

Tool 50 comprises an outer tube 52 and an inner tube 54 that is slightly smaller in diameter. The tubes 52 and 54 are concentrically mounted, and can be rotated relative to one another. A knob 56 is secured to the inner tube, at its upper end, so that rotational movement can be imparted thereto. A hand grip 58 is positioned about the outer tube near its upper end, and a series of markings, which function as a depth gauge 60, is scored, or engraved, onto the outer tube below the hand grip. Locator pins 62, 64 are formed at diametrically opposed locations at the lower end of the outer tube 52.

As shown in FIGS. 4 and 5, pins 62, 64 fit into holes 34, 36 in the obturator plate 30 on the tubular body 22 establish a fixed relationship between cement plug 20 and installation tool 50. A hexagonal recess 66 is formed in the lower face 68 of the inner tube 54, as shown in FIG. 4. Recess 66 is configured to receive the head 40 of bolt 38. When the pins 62, 64 are located in the holes 34, 36, the head of the bolt is snugly received in recess 66. Consequently, when knob 56 is rotated, a torquing force is delivered by inner tube 54 to the bolt 38 which, in turn, draws tapered conical plug 24 upwardly into the tubular body 22 and forces the resilient fingers 28 outwardly. The cooperative interaction between tapered conical plug 24 and fingers 28 is shown, progressively, in FIGS. 5 and 6.

Figure 8:
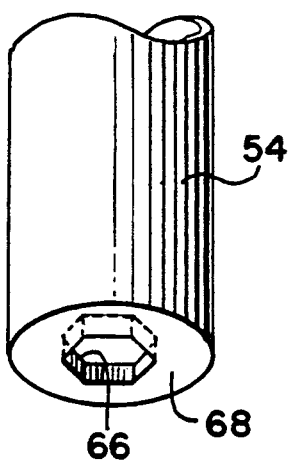
FIG. 8 is a perspective view of the lower end of the inner tube of the insertion tool shown in FIG. 4, such view showing the recess adapted to receive the head of the bolt for the cement plug.
Figure 9:
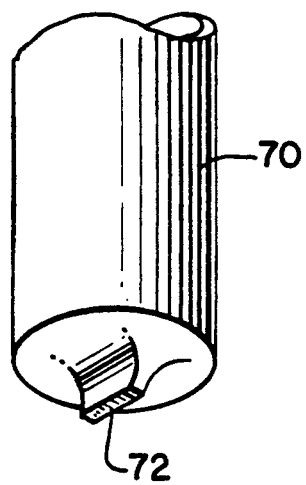
FIG. 9 is a perspective view of an alternative embodiment of the inner tube of the insertion tool shown in FIG. 4, such view showing a screwdriver blade adapted to fit into a slot in the head of the bolt for the cement plug.

Additional details of installation tool 50 are depicted in FIGS. 7-9, on an enlarged scale. FIG. 7 shows outer tube 52 with the pair of pins 62, 64 extending therebelow. Inner tube 54, which fits within tube 52, is visible in FIG. 8, and the lower surface 68 and the hexagonal recess 66 in the tube 52 are clearly shown. The recess is sized and configured to receive the head 40 of bolt 42, and the pins fit into holes 34, 36 in obturator plate 30.

A different inner tube 70 may be substituted for inner tube 54 of installation tool 50, as shown in FIG. 9. In this alternative embodiment of the insertion tool, inner tube 70 terminates in a screwdriver blade 72; such blade would be utilized if a bolt 38 with a slotted head were used in lieu of the hexagonal head 40 usually employed on bolt 42. Blade 72 may have tapered sides so that it fits securely into the slot in the head of the bolt.

Figure 10:
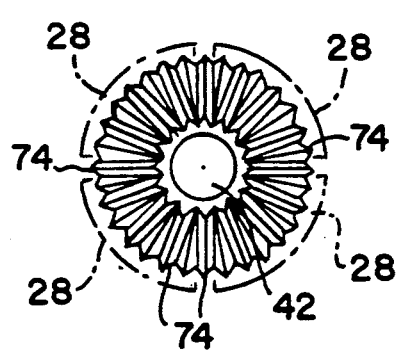
FIG. 10 is a bottom plan view of an alternative embodiment of the tapered conical plug and the resilient fingers defined at the bottom of the tubular body of the cement plug, the conical plug having a plurality of serrations formed on its outer surface.
Figure 11:
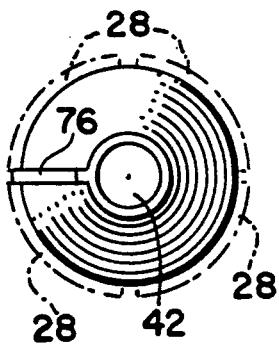
FIG. 11 is a bottom plan view of another alternative embodiment of the tapered conical plug and the resilient fingers defined at the bottom of the cement plug, the conical plug having an orienting tab on its outer surface.
Figure 12:
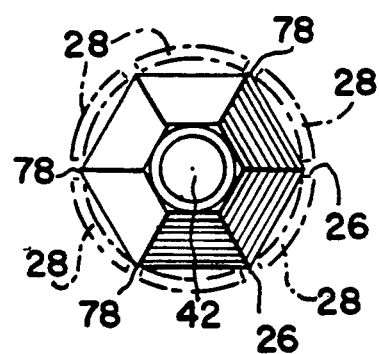
FIG. 12 is a bottom plan view of yet another alternative embodiment of the tapered conical plug and the resilient fingers defined at the bottom of the cement plug, the conical plug having a series of sharp corners formed on its exterior surface.

FIGS. 10-12 depict other structural features that may be employed to increase the effectiveness of cement plug 20. To illustrate, FIG. 10 shows a plurality of serrations formed on the exterior of tapered conical plug 24. The serrations 74 engage the interior surface of the tubular body and prevent the tapered conical plug 24 from slipping, in a rotational sense, relative to the fingers 28. Thus, the bolt advances the tapered conical plug 24 positively, axially upwardly, into the interior of the tubular body.

FIG. 11 depicts an aligning tab 76 situated on the exterior surface of tapered conical plug 24. Tab 76 fits into the axial slit between adjacent fingers 28 and orients tapered the conical plug 24 relative to tubular body 22. The plug 24 is keyed to the tubular body and does not slip when the plug 24 is drawn up axially into the body by the rotational forces imposed upon bolt 38.

While the number of axial slits 26 formed in the tubular body 22 of the cement plug 22 can vary, provided that a minimum of three is maintained, FIG. 12 suggests that six slits 26 can be made to form six fingers 28 at the lower end of the tubular body 22 of the cement plug. Similarly, six sharp corners 78 are formed on the exterior surface of tapered conical plug 24, and each corner is aligned with a slit 26. The sharp corners 78 fit into slits 26 and spread the resilient fingers 28 apart for enhanced gripping power, while preventing the tapered conical plug from slipping while being drawn upwardly by bolt 42.

CYCLE OF OPERATION

Although the installation and operation of cement plug 20 is believed to be readily apparent from the foregoing description, a summary may be advantageous. Pins 62, 64 on the insertion tool are engaged within holes 34, 36 in the obturator plate 32, so that the head 40 of the threaded bolt fits into recess 66 in the lower face 68 of the inner tube 54 of the insertion tool. The lower end of threaded bolt 42 is secured within axial bore 46 of tapered conical plug 24 so that the plug is retained at the lower end of the tubular body 22 of the cement plug.

The insertion tool is manipulated into the medullary canal, to the desired depth for the cement plug, as indicated by the scale 60 on the exterior of the tool 50. When the cement plug attains the desired depth, the surgeon rotates the handle 56 on the tool, thus rotating the inner tube 54 and imparting a torquing force to threaded bolt 42. As the bolt is rotated, the coaction of threads 42 with threads 46 on the interior of the bore in tapered conical plug 24, draws the plug 24 upwardly through the lower end of the tubular body 22 of the cement plug and into the interior thereof. The tapered configuration of plug 24 forces resilient fingers 28 outwardly into engagement with the wall defining the medullary canal, as shown in FIG. 6.

The obturator plate 30 extends transversely across the medullary canal, and serves as a secondary line of engagement. Plate 30 receives the weight and force of the pressurized cement, and may even bow slightly under such loading, also as shown in FIG. 6. The plate prevents cement, or debris, from travelling therepast and contacting the resilient fingers 28. Thus, if need be, the cement plug may be readily re-adjusted, for the cement has not contaminated the resilient fingers or bonded same to the wall of the medullary canal.

While a preferred embodiment of the invention has been described in detail, and some modifications to the insertion tool and the cement plug have been suggested, other modifications, alterations, and revisions may occur to the skilled artisan in the broad field of medical prosthetics in which this invention finds particular application. Consequently, the appended claims should not be limited to their literal terms, but should be construed broadly in a manner consistent with the significant contribution to the useful arts and sciences.

We claim:

1. A cement plug adapted to be used in a medullary canal, said plug comprising:
   a) a tubular body executed in a biocompatible plastic,
   b) said body having an upper end and a lower end,
   c) said body being slit axially in several parallel areas extending upwardly from its lower end to define a plurality of resilient fingers,
   d) an obturator plate located at the upper end of said body and extending perpendicular thereto,
   e) said plate having a centrally located aperture,
   f) a tapered conical plug that fits into the lower end of said tubular body,
   g) said tapered conical plug having a threaded axial bore extending therethrough;
   h) a bolt having an enlarged head and an elongated shank, said shank having threads along its exterior surface,
   i) the head of said bolt resting upon said obturator plate with the shank extending axially through said tubular body and into the threaded bore of said tapered conical plug,
   j) whereby the application of a rotational force to the head of said bolt in a first direction draws said tapered conical plug upwardly into said tubular body and forces said resilient flexible fingers outwardly to engage the wall of a surrounding medullary canal at several spaced points.

2. A cement plug as defined in claim 1 wherein said tubular body is executed in non-porous plastic.

3. A cement plug as defined in claim 1 wherein said tubular body is slit at three, equally spaced, areas.

4. A cement plug as defined in claim 1 wherein each slit extends upwardly for more than half the axial length of the tubular body.

5. A cement plug as defined in claim 1 wherein said obturator plate is annular in shape when viewed from above.

6. A cement plug as defined in claim 5 wherein the diameter of said obturator plate is significantly greater than the diameter of said tubular body, the diameter of said obturator plate being selected to match the size of the medullary canal.

7. A cement plug as defined in claim 1 wherein serrations are formed on the exterior of said tapered conical plug to facilitate spreading the resilient fingers on said tubular body.

8. A cement plug as defined in claim 1 wherein the exterior surface of said tapered conical plug is divided into several distinct faces, the adjacent faces meeting at a sharp corner, and the number of corners being equal to the number of axial slits in said tubular body.

9. A cement plug as defined in claim 1 wherein a tab is formed on the outer surface of said tubular body of said plug, said tab cooperating said axial slits in said tubular body to prevent rotation of said tapered conical plug as said tapered conical plug enters said tubular body.

10. In combination, a cement plug adapted to be used in a medullary canal, and a manually operable tool for positioning and locking said cement plug in a fixed location within the medullary canal,
1) said plug comprising:
   a) a tubular body executed in a bio-compatible plastic,
   b) said body having an upper end and a lower end,
   c) said body being slit axially in several parallel areas extending upwardly from its lower end to define a plurality of resilient fingers,
   d) an obdurator plate located at the upper end of said body and extending perpendicular thereto,
   e) said plate having a centrally located aperture,
   f) a tapered conical plug that fits into the lower end of said tubular body,
   g) said tapered conical plug having a threaded axial bore extending therethrough,
   h) a bolt having an enlarged head and an elongated shank, said shank having threads along its exterior surface,
   i) the head of said bolt resting upon said obdurator plate with the shank extending axially through said tubular body and into the threaded bore of said tapered conical plug,
   j) a plurality of locator holes formed in said obdurator plate,
2) said insertion tool comprising:
   a) an inner tubular member,
   b) an outer tubular member, said tubular members mounted concentrically to enable relative movement therebetween,
   c) a plurality of aligning pins projecting from the lower end of said outer tube for insertion into said locator holes in said obdurator plate,
   d) means defined in the lower surface of said inner tubular member to receive the head of said bolt therein, and
   e) manually operable means at the upper end of said inner tubular member for rotating same to deliver a torquing force to the head of said bolt to thereby draw said tapered conical plug into said tubular body and force the resilient fingers outwardly into secure engagement within the medullary canal, with the obturator plate serving as a barrier across the medullary canal above said fingers.

11. A cement plug and a manually operable tool as defined in claim 10 wherein the head of said bolt is polygonal in shape, and said inner tube of said tool has a lower, transversely extending surface with a polygonal recess to fit over the head of said bolt.

12. A cement plug and a manually operable tool as defined in claim 10 wherein the head of said bolt has a slot formed therein, and said inner tube of said tool has a depending screwdriver blade that fits into said slot on said bolt.

13. A cement plug and a manually operable tool as defined in claim 10 wherein said locator holes in said obdurator plate extend only partially through said plate, said aligning pins in said tool being equal in number to said locator holes.

14. A cement plug and a manually operable tool as defined in claim 10 wherein a pair of locator holes in said obdurator plate are spaced diametrically apart from each other.

15. A cement plug and a manually operable tool as defined in claim 10 wherein a depth gauge is located on the exterior of said outer tube of said tool to indicate the depth of insertion of the tool into the medullary canal.

16. A cement plug adapted to be used in a medullary canal, said plug comprising:
   a) a tubular body (22) executed in a biocompatible plastic,
   b) said body having an upper end and a lower end,
   c) said body being slit axially upwardly from its lower end, at several spaced areas, to define a plurality of resilient fingers (28),
   d) a tapered conical plug (24) that fits into the lower end of said tubular body,
   e) said tapered conical plug having a threaded bore extending axially therethrough,
   f) a bolt (38) having an enlarged head (40) and an elongated shank (42), said shank having threads (44) defined along its exterior surface,
   g) the application of a rotational force to the head of said bolt in a first direction drawing said conical plug upwardly into said tubular body and forcing said resilient fingers outwardly to engage the wall of the surrounding medullary canal at several spaced points (see FIG. 5); and
   h) the invention being characterized by an obturator plate (30) located at the upper end of said tubular body and perpendicular thereto, said plate being greater in transverse dimensions than said body and extending across the medullary canal to serve as a barrier for preventing debris in the medullary canal from passing therebeyond (see FIG. 6).

17. A cement plug as defined in claim 16 wherein said obdurator plate is substantially annular in shape when viewed from above (see FIG. 2) and contacts the medullary canal around its perimeter, the obdurator plate being selected to be sufficiently rigid to engage the bone defining the medullary canal, thereby functioning as a secondary locking member for said plug and augmenting the engagement forces of said resilient fingers (see FIG. 6).

18. A cement plug as defined in claim 17 wherein said obdurator plate may be sufficiently flexible to bow under the weight of the debris and bone cement in the medullary canal while still maintaining continuous contact with the bone defining the medullary canal.

19. A cement plug as defined in claim 18 wherein said obdurator plate has a central aperture to allow the shank of said bolt to pass therethrough, the head of said bolt resting on said obdurator plate when said cement plug is installed in the medullary canal (see FIG. 5).

* * * * *